United States Patent [19]

Roge

[11] 4,321,926
[45] Mar. 30, 1982

[54] INSERTION DETECTING PROBE AND ELECTROLYSIS SYSTEM

[76] Inventor: Ralph R. Roge, 6426 S. Richmond Ave., Clarendon Hills, Ill. 60514

[21] Appl. No.: 30,602

[22] Filed: Apr. 16, 1979

[51] Int. Cl.³ .................................... A61B 17/41
[52] U.S. Cl. ................................... 128/303.18
[58] Field of Search ............. 128/303.13, 303.14, 128/303.17, 303.18, 419 R

[56] References Cited

U.S. PATENT DOCUMENTS

| | | | |
|---|---|---|---|
| 2,417,530 | 3/1947 | Weiser | 128/303.13 |
| 2,516,882 | 8/1950 | Kalom | 128/303.18 X |
| 2,700,975 | 2/1955 | Hopfinger et al. | 128/303.18 |
| 2,994,324 | 8/1961 | Lemos | 128/303.18 |
| 3,054,405 | 9/1962 | Tapper | 128/303.18 |
| 3,152,590 | 10/1964 | Zurdo et al. | 128/303.18 |
| 3,315,678 | 4/1967 | Donelson | 128/303.18 |
| 3,359,982 | 12/1967 | Guiorguiev | 128/303.18 |
| 4,124,028 | 11/1978 | Gallo | 128/419 R |
| 4,216,775 | 8/1980 | Cottingham | 128/303.18 |

FOREIGN PATENT DOCUMENTS

| | | |
|---|---|---|
| 2540968 | 3/1977 | Fed. Rep. of Germany ........................ 128/303.17 |
| 897961 | 6/1962 | United Kingdom ........... 128/303.14 |

*Primary Examiner*—Lee S. Cohen
*Attorney, Agent, or Firm*—Neuman, Williams, Anderson & Olson

[57] ABSTRACT

An electrolysis system having a shortwave power source automatically energized in response to insertion of a cauterizing probe needle into the patient's skin pore or follicle. The system includes a conductive probe and detector circuit which senses a current path being closed by contact of the needle with the patient and a power gating system which applies the cauterizing energy to the needle in controlled amounts and at a preselected time subsequent to the insertion of the needle into the pore.

7 Claims, 2 Drawing Figures

U.S. Patent
Mar. 30, 1982
4,321,926
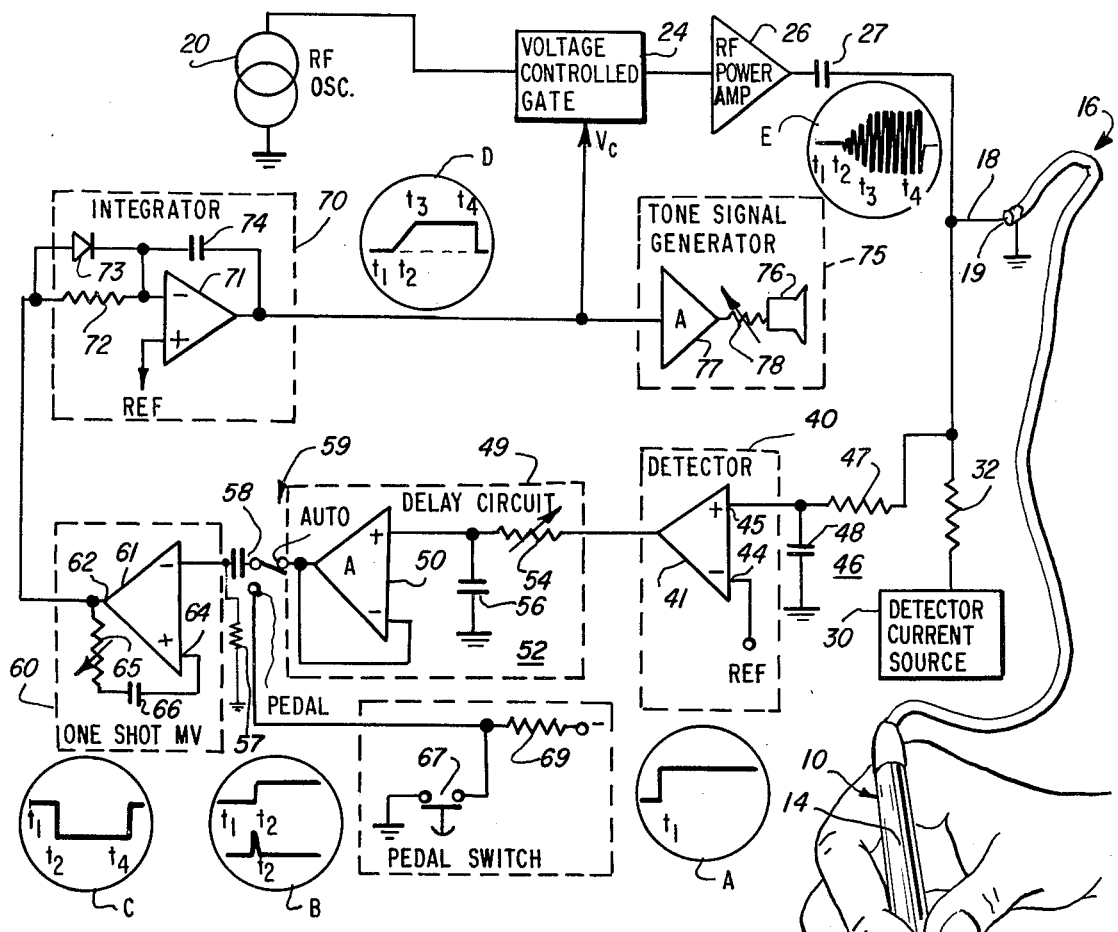
FIG. 1
FIG. 2
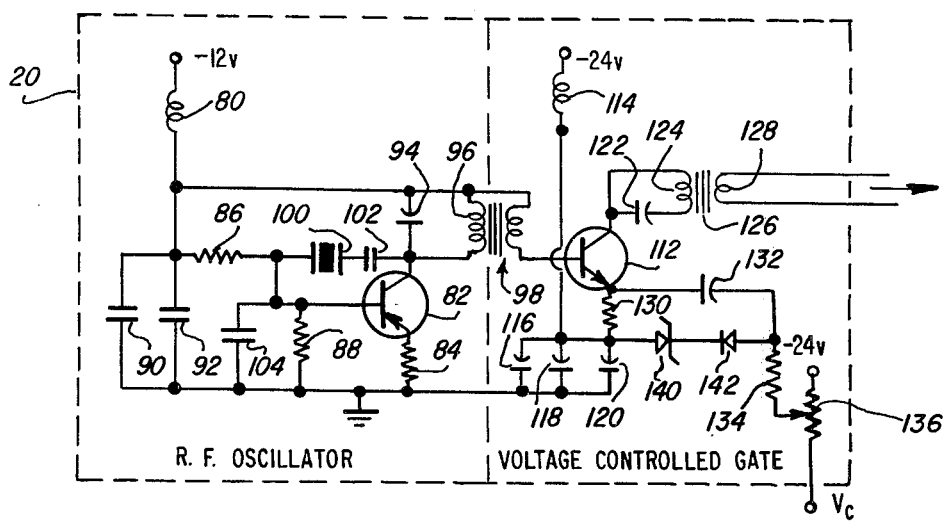

INSERTION DETECTING PROBE AND ELECTROLYSIS SYSTEM

FIELD OF THE INVENTION

This invention is related generally to electrolysis systems and more particularly to electrolysis systems wherein various functions are automated.

BACKGROUND OF THE INVENTION

Electrolysis systems have been used for many years for permanent removal of hair from a patient's skin. Most electrolysis systems developed in the past and being used at present include a needle for selectively applying electrical energy to the patient's hair follicle after insertion of the needle into the follicle pore. A foot pedal has traditionally been used by the operator to control current flow through the needle once the operator feels that the needle is fully inserted into the pore. This has required a subjective determination on the part of the operator and a great amount of skill. While the shortwave energy, normally in the RF frequency range, could be controlled in duration by the pedal itself, more typically this energy is controlled to be a predetermined burst, i.e., limited in time and magnitude. Pilot lamps have been provided on numerous machines to allow the operator to determine when energy ceases to be applied. The amount of the energy applied to the needle has usually been preset and constant in magnitude, although a control has normally been provided on the panel of the machines for preselecting that energy level.

While modest attempts to automate the electrolysis process have been made, such as through the automatic limiting of the period during which energy is applied, most systems continue to require substantial manipulation and dexterity on the part of the operator and most systems still involve substantial discomfort to the patient and a danger of skin damage when in the hands of an inexperienced or unskilled operator.

BRIEF SUMMARY OF THE INVENTION

The electrolysis system of the present invention overcomes the drawbacks and deficiencies of the prior systems described above by providing automated control of the many decisions normally made by the operator on a subjective basis during the pore cauterizing operation. It is, therefore, a primary object of the present invention to free the operator from many of the mental and physical manipulations presently attendant to the electrolysis process. It is a more specific object of the present invention to provide an electrolysis machine which frees the operator from the drudgery of depressing a foot pedal or similar device while giving the operator appropriate signals indicative of the performance of the machine.

It is a further object of the present invention to allow the operator to perform consistent and rapid cauterization operations while minimizing the discomfort to the patient.

The foregoing and other objectives are achieved through the provision of a system which utilizes an electronic detector to determine when the needle makes contact with the skin. A shortwave or RF signal generator is selectively gated to apply cauterizing electrical energy to the needle after a predetermined delay subsequent to the detection of needle insertion, and the amount of energy applied to the needle is gradually increased from a low magnitude to minimize the discomfort to the patient. Additional means are provided for generating an audible tone during application of energy to the needle so as to signal the operator when it is time to move to the next hair follicle.

Other objects and advantages of the present invention will become apparent upon reading of the following detailed description and upon reference to the drawings.

BRIEF DESCRIPTION OF THE DRAWINGS

FIG. 1 is a circuit diagram, partially in block form, of the electrolysis system of the present invention showing the principle circuit functions.

FIG. 2 is a circuit schematic showing additional detail with respect to the oscillator and voltage controlled gate circuits shown in the block diagram of FIG. 1.

DESCRIPTION OF THE ILLUSTRATED EMBODIMENT

Turning first to FIG. 1, the electrolysis system there depicted includes a probe which serves the dual functions of a needle providing point contact for cauterizing the patient's skin and a conductive detector for determining when a current path is closed between the skin and the needle. To this end, the probe 10 depicted in FIG. 1 includes a central conductive needle 12 which is made of highly conductive metal and sharpened for insertion into a patient's hair follicle or pore. A conductive outer sleeve 14 is spaced from and surrounds the central needle 12. The needle 12 is held in place and is electrically insulated from the conductive sleeve 14 by a central probe body 15 of high dielectric material such as plastic or the like. Emanating from the rear end of the probe 10 is an electrical cable 16, typically of the coaxial type, having a central conductor 18 which is attached to the needle 12 internal to the probe 10 in a permanent manner such as by soldering or the like. The cable 16 also has a conductive outer sheath 19 which is electrically insulated from the central conductor 18 and is coupled to the conductive sleeve 14 of the probe 10.

For the purpose of providing electrical energy to the needle 12 sufficient to cauterize a hair follicle, the system of FIG. 1 includes a power source 20 which is selectively gated to the central conductor of the probe 10 by a voltage controlled gate 24 in a manner to be hereinafter described. The cauterization of skin can be accomplished with various types of electrical energy from direct currents to very high frequency alternating current. It has been found preferable with the present invention to utilize as the power source 20 a radio frequency (RF) oscillator producing shortwave electrical energy. Whereas low frequency or DC current, for proper cauterization, must be applied for long periods of time approaching five minutes, shortwave current can accomplish the objective in a fraction of a second if properly controlled in magnitude. Coupled between the voltage controlled gate 24 and the probe 10 is an RF power amplifier 26 whose output is capacitively coupled via a capacitor 27 to the central conductor 18 of the cable 16.

To automate the function normally provided by the foot pedal in an electrolysis system, the apparatus shown in FIG. 1 includes means for sensing the insertion of the conductive needle 12 into the patient's skin and thereafter, after a suitable delay, automatically actuating the voltage controlled gate 24 to apply RF power to the needle 12. To this end, a detector circuit is provided which includes a source of low magnitude electrical current 30 which supplies its current to the central conductor 18 of the cable 16, and thus to the needle 12, through a dropping resistor 32. The power source 30 may be typically a 24 volt negative DC power supply. The coupling capacitor 27 connected to the output of the RF power amplifier 26 prevents the DC power source 30 from interfering with normal operation of the power amplifier 26.

The current supplied to the probe from the power source 30 is for detection purposes only, and is controlled in magnitude so as to be able to pass through the skin of the patient from the needle 12, through the skin of the operator and back to the outer conductive sleeve 14 of the probe 10 and thereafter to ground via the outer conductive sheath 19 of the coaxial cable 16. For the purpose of detecting the closure of the aforesaid circuit by contact of the probe needle 12 to the patient's skin, a detector circuit 40 is provided. As shown, the detector is depicted as an operational amplifier 41 which is referenced to a DC reference potential (Ref) via an input terminal 44 thereof while its non-inverting input terminal 45 is coupled through an RF trap 46 to the central conductor 18 of the probe coaxial cable 16. The RF trap 46, functionally depicted as a series resistor 47 and shunt capacitor 48, serves to protect the amplifier 41 from actuation by the RF energy applied to the central conductor 18 of the probe 14 by the oscillator 20 during the operational cycle of the system. As such, the detector amplifier 41 responds only to the low frequency or DC current which results from application of the needle 12 to a hair follicle while the patient and operator are in skin contact.

It is not desirable to immediately energize the probe needle 12 with RF energy upon its initial contact with the skin, since the probe should preferably be inserted an additional fraction of an inch into the pore prior to cauterization. Therefore, to prevent immediate actuation of the cauterizing current, there is provided a delay circuit 49 consisting of a unity gain operational amplifier 50 having its input controlled by an RC delay network 52 which is functionally represented by a series potentiometer 54 and shunt capacitor 56 for simplicity of description. The delayed detector output signal emanates from the output of the operational amplifier 50 and is thereafter differentiated by a capacitor 58 operating in conjunction with a resistor 57 to provide a sharp pulse which occurs a predetermined period after initial contact of the needle with the skin so as to allow the probe to be fully inserted to the proper depth.

A mode selector switch 59 is coupled between the amplifier 50 and the capacitor 58 to allow selection between an automatic mode (AUTO) disclosed thus far and a manual (PEDAL) mode described below.

The pulse derived from the differentiating capacitor 58 is applied to a one-shot multivibrator circuit 60 functionally depicted as a operational amplifier 61 having its output terminal 62 coupled to its non-inverting input terminal 64 via a feedback capacitor 66 in a typical manner. The one-shot multivibrator 60 controls the time period during which cauterizing current will be supplied to the needle 12. The time constant or output pulse width from the one-shot circuit 60 is made adjustable by a potentiometer 65 located in the feedback path in series with the capacitor 66 and controlled by a knob on the operator's control panel (not shown). Typically the pulse width is adjustable to provide a burst of energy of from 100 ms to 2 seconds or more.

To allow for manual actuation of the system in lieu of the automatic actuation provided by the detector circuit, the embodiment of FIG. 1 includes a PEDAL triggering circuit having a normally open switch 67 which may be actuated in a variety of manual ways, but preferably by the operator's foot. The switch 67 selectively grounds one end of a resistor 69 connected to a power supply, the resulting voltage change being coupled to the PEDAL contact of the mode selector switch 59 through a capacitor 58. In the PEDAL mode, therefore, closing of the switch 67 creates an instantaneous voltage change which is differentiated by the capacitor 58 and resistor 57 to trigger the multivibrator circuit 60 in the same manner as provided by the detector delay circuit 49 in the AUTO mode.

It has been found desirable to apply the RF or short-wave energy to the needle 12 in a gradually increasing rather than step-function fashion. Greater patient comfort is achieved in this manner due to the fact that the resistance of the skin within the pore increases as cauterization continues such that the highest levels of current are necessary for cauterization only after the cauterization period has begun. Much lower, and hence more comfortable, levels of current can achieve the necessary result during the initial portions of the application of energy to the skin. For this reason the system shown in FIG. 1 includes a ramp generator or integrating circuit 70 coupled between the output of the one-shot multivibrator 60 and the input to the voltage controlled gate 24. The integrator 70 is functionally shown as including an operational amplifier 71 having an input circuit consisting of a resistor 72 and diode 73 in parallel coupled to the inverting input terminal of the operational amplifier 71 with a feedback capacitor 74.

The integrator 70 provides a gradual increase in the voltage applied to control the gate 24 and also drives a tone signal generator 75 consisting of a voltage controlled tone generator 76 and an associated amplifier 77 which enables the operator to determine when the energy is being applied to the needle 12 for cauterization. A volume control potentiometer 78 allows the operator to manually select the desired tone volume.

The voltage controlled gate 24 may be any of a variety of devices or circuits which pass an analog input signal in proportion to a varying signal at a control terminal $V_C$. An effective device which has been used for this purpose is a variolosser. Devices of this type exhibit a signal loss in proportion to an applied voltage or current.

However, the preferred circuit for the voltage controlled gate 24 is that shown in FIG. 2 together with a suitable circuit for the RF oscillator 20. Turning first to the oscillator circuit, power for the circuit is provided by a negative DC source, typically at $-12$ volts, through an inductor or choke 80. The oscillator is of the feedback type and includes a transistor 82 biased in a common emitter configuration. The emitter is coupled to ground through a resistor 84. The base of the transistor 82 is biased by a resistance 86 coupled to the DC negative source through the choke 80 and by a resistor 88 coupled to ground to provide a voltage division network. The bias potential across the resistors 86 and 88 is maintained by a pair of capacitors 90 and 92 connected in parallel. The collector load for the transistor 82 is an LC tank circuit consisting of a capacitor 94 connected in parallel with the input winding 96 of a coupling transformer 98. For the purpose of controlling the frequency of oscillation within the circuit, there is provided a crystal 100 coupled in series with a capacitor 102 in the collector-to-base feedback circuit of the transistor 82. An additional capacitor 104 is coupled between the base electrode of the transistor 82 and ground to complete the regeneration circuit. The crystal 100 was chosen to be 13.56 megahertz in frequency.

Turning now to the voltage controlled gate circuit 24, the input signal from the oscillator is received from the output winding of the coupling transformer 98 and applied to the base of a transistor 112 of the NPN variety. Bias potential for the emitter of the transistor 112 is provided by a DC power source nominally of −24 volts DC. The power source is coupled through an inductor or choke 114 and regulated by a bank of parallel capacitors 116, 118 and 120. The output from the transistor 112 is taken from the collector of the transistor 112 through an LC circuit consisting of a capacitor 122 which is coupled to ground in parallel with the input winding 124 of a coupling transformer 126. The output from the voltage controlled gate circuit 24, accordingly, appears across an output winding 128 of the coupling transformer 126.

In order that it may perform as a voltage controlled amplifier, the transistor 112 has its emitter current, and hence its transconductance, controlled by the external voltage derived from the ramp generator or integrator 70 shown in FIG. 1. The quiescent bias circuit for the emitter of the transistor 112 includes a dropping resistor 130 coupled to the −24 volt DC negative supply through the inductor 114. Variable control for the transconductance of the transistor 112 is derived through a series circuit consisting of a capacitor 132, a resistor 134 and one side of a potentiometer 136 which is connected between the 24 volt negative supply and the voltage control terminal designated $V_C$ in FIGS. 1 and 2. In order to prevent an overswing in the signal applied to the emitter of transistor 112, the emitter bias circuit is clamped by a pair of series connected diodes including a zener diode 140 and a conventional diode 142 coupled between the negative 24 volt source and the bias resistor 134.

By adjusting the position of the wiper arm on the potentiometer 136, the sensitivity or the transconductance of the transistor 112, and hence the intensity of the RF power output from the gate circuit 24, can be accurately controlled.

The voltage controlled gate operates in the following manner. In the quiescent condition the input voltage on the terminal $V_C$ is close to −24 volts potential so that the transconductance of the transistor 112 is effectively zero. As the detector circuit (or foot switch 67) becomes activated, the control potential on the terminal $V_C$ linearly increases in the positive direction, the rate of increase being controlled by the setting of the potentiometer 136 from a knob on the face of the control panel (not shown). As such, the current available to the emitter of the transistor 112 increases in proportion to the voltage at the terminal $V_C$, thereby permitting a gradually increasing amount of the oscillator output signal from the transformer 98 to pass to the gate output winding 128. The envelope of the output signal on the output winding 128 thereafter corresponds to the applied voltage at the control terminal $V_C$ and falls to zero as that applied voltage returns to ground potential at the conclusion of the desired cauterizing period.

To briefly summarize the operation of the electrolysis system as a whole, reference is made to the signal diagrams A, B, C, D and E shown on FIG. 1. Prior to using the system, the operator adjusts the appropriate controls available to him on his control panel as follows. The time delay between the initiation of skin contact by the needle 12 and the beginning of the RF burst is adjusted by manual control of the potentiometer 54 in the delay circuit 49. The time duration of the RF burst is manually controlled by adjustment of the potentiometer 65 in the feedback circuit of the one-shot multivibrator circuit 60. The intensity or amplitude of the applied RF signal is controlled by manual adjustment of the potentiometer 136 in the voltage controlled gate circuit 24 shown in FIG. 2. Finally, the volume of the audible output during cauterization is controlled by manual adjustment of the potentiometer 78 in the tone signal generator 75. All of these controls are available to the operator on the control panel.

With the foregoing variables adjusted to the desired levels, the operator inserts the needle 12 of the probe 10 into the skin pore. As soon as the needle touches the skin, current flows from the detector current source 30 and a voltage is developed at the non-inverting input terminal 45 of the detector 40 which exceeds the reference voltage at the input terminal 44. The output of the detector 40, depicted in the signal diagram A, abruptly changes upon contact with the skin at the time $t_1$. The signal from the detector is delayed for a short period, typically 200 to 400 milliseconds, by the delay circuit 49 as shown by the upper trace of the signal diagram B. Thereafter, the delayed detector pulse is differentiated in the capacitor 58 as shown in the lower trace of the signal diagram B, and a narrow triggering spike is created at the time $t_2$. The triggering spike from the differentiating capacitor 58 fires the one-shot multivibrator 60 for a time period of from 100 milliseconds to 1 second, depending upon the setting of the timing potentiometer 65. At the end of this time period, designated $t_4$ in the signal diagram C, the output of the one-shot multivibrator 60 returns to its quiescent state. As the output of the multivibrator 60 changes at the time $t_2$, the integrator circuit 70 begins to produce a gradually increasing output signal as shown in the signal diagram D. The integrator output signal increases for approximately 20 milliseconds, or until the time $t_3$, and thereafter remains constant until the time $t_4$. The output signal from the integrator 70 creates an audible tone from the tone signal generator 75 at a volume determined by the setting of the potentiometer 78. The voltage controlled gate 24 responds to the output signal from the integrator 70 by gating the output signal from the oscillator 20 to the probe during the period beginning at the time $t_2$ and ending at the time $t_4$ as shown in the signal diagram E. During the period from $t_2$ to $t_3$ during which the integrator output increases, the output from the gate 24 has a correspondingly increasing envelope. During the period from $t_3$ to $t_4$ during which the integrator output is constant, the output from the gate 24 remains at a fixed constant level. At the time $t_4$ the gate 24 effectively closes despite the fact that the operator is normally still in skin contact with the patient. The cauterization period is completed and both the input and output from the integrator circuit return to their quiescent state. The operator then removes the needle 12 and moves to the next pore.

As noted above, in lieu of using the detector 40 and delay circuit 49, the one-shot multivibrator circuit 60 may be triggered from the foot switch 67 when the system is in the PEDAL mode rather than the AUTO mode as determined by the panel switch 59. In either mode the effect on the comfort of the patient is the same since the RF energy is applied in a gradually increasing amount until cauterization of the patient's pore allows for the full magnitude of the RF current without excessive patient discomfort.

From the foregoing, it will be apparent that there has been brought to the art a new and improved electrolysis system which maximizes the speed of operation, creates a degree of comfort for the patient heretofore unavailable, and which requires a minimum amount of skill and subjective decision making on the part of the operator.

While a particular embodiment of the invention has been shown, it will be understood, of course, that the invention is not limited thereto, since modifications may be made by those skilled in the art, particularly in light of the foregoing teachings. It is, therefore, contemplated by the appended claims to cover any such modifications as incorporate those features which constitute the essential features of these improvements within the true spirit and scope of the invention.

I claim as my invention:

1. A system for selectively cauterizing skin pores comprising:
   a probe having a conductive central needle adapted for insertion into a patient's skin pore and a conductive outer sleeve portion adapted to be handheld by an operator who is in electrical contact with the patient;
   an electrical power source for producing shortwave electrical energy suitable for skin cauterization;
   low current detector means operatively associated with said central needle and outer sleeve of the probe for sensing when low current electrical contact is made between the central needle of the probe and the patient's skin and producing an electrical signal in response thereto;
   means response to said electrical signal from said detector means for coupling said shortwave electrical energy to the probe central needle for cauterization of the skin pore;
   and means for controlling the duration of application of said electrical shortwave energy to said central needle.

2. A system according to claim 1 further including delay circuit means associated with said detector means for initiating the coupling of said shortwave electrical energy to the probe central needle at a predetermined delay interval subsequent to the occurrence of said electrical signal from the detector means.

3. A system according to claim 1 wherein said coupling means includes a voltage controlled gate and wherein said system further includes a ramp generator coupled between said detector means and said voltage controlled gate so as to gradually increase the shortwave electrical energy passed through said gate after initiation thereof by said electrical signal from said detector means.

4. A system for selectively cauterizing skin pores comprising:
   a probe having a conductive central needle adapted for insertion into a patient's skin pore and a conductive outer sleeve portion adapted to be handheld by an operator who is in electrical contact with the patient;
   an electrical power source for producing shortwave electrical energy suitable for skin cauterization;
   low current detector means operatively associated with said central needle and outer sleeve of the probe for sensing when a low current path is completed between the central needle of the probe and the outer sleeve through the patient's skin and the operator's skin and for producing an electrical signal in response thereto;
   means responsive to said electrical signal from said low current detector means for coupling said shortwave electrical energy to the probe central needle for cauterization of the skin pore.

5. A system according to claim 4 for selectively cauterizing skin pores wherein said low current detector means further includes a direct current source in series circuit with said central needle and the conductive outer sleeve and means for sensing the flow from said current source resulting from contact of the central needle with the patient's skin while the patient's skin is in contact with the operator, said low current detector means further including a filter means for distinguishing between said direct current and the higher frequency cauterizing energy so that the electrical output signal from said detector means occurs only in response to the sensing of said direct current.

6. A system according to claim 5 wherein said shortwave electrical energy is at an RF frequency and wherein said filter means is an RF trap.

7. A method for controlling the application of shortwave electrical energy to a patient's skin pore through a probe having a conductive central needle adapted to be inserted into the pore and an outer conductive sleeve portion adapted to be held by the operator, said method consisting essentially of:
   applying a first electrical signal of low current to said needle prior to insertion of the needle into the skin;
   detecting the initiation of electrical contact between said needle and the skin by sensing the portion of said first electrical signal passing from the needle through the patient's skin, the operator and the conductive outer sleeve being held by said operator;
   generating a gate control signal beginning after a predetermined time interval subsequent to said detection of contact between the needle and the skin; and
   controlling the application of a second electrical signal of shortwave electrical energy to said needle in accordance with the magnitude and duration of said gate control signal, said first electrical signal being relatively small so as to prevent discomfort to the patient and said second electrical signal being of substantially greater magnitude than said first electrical signal so as to create cauterization of the skin pore as it passes from the needle.

* * * * *